United States Patent [19]
Stio

[11] Patent Number: 6,165,337
[45] Date of Patent: Dec. 26, 2000

[54] SEMI-DRY ELECTROPHORESIS APPARATUS AND METHOD

[75] Inventor: Tom Stio, Bloomington, Ind.

[73] Assignee: Shelton Scientific Manufacturing, Inc., Shelton, Conn.

[21] Appl. No.: 09/220,569

[22] Filed: Dec. 23, 1998

[51] Int. Cl.[7] .................................................. G01N 27/26
[52] U.S. Cl. ........................ 204/456; 204/606; 204/616; 204/466
[58] Field of Search ................................... 204/456, 460, 204/606, 616, 414, 614; 436/515

[56] References Cited

U.S. PATENT DOCUMENTS

| | | | |
|---|---|---|---|
| 3,407,133 | 10/1968 | Oliva et al. | 204/616 |
| 4,391,688 | 7/1983 | Hamelin | 204/461 |
| 4,954,236 | 9/1990 | Kushner et al. | 204/299 |
| 5,449,446 | 9/1995 | Verma et al. | 204/612 |
| 5,582,702 | 12/1996 | Cabilly et al. | 204/456 |
| 5,637,202 | 6/1997 | Harrington et al. | 204/469 |
| 5,891,625 | 4/1999 | Buchardt et al. | 435/6 |

*Primary Examiner*—Jill Warden
*Assistant Examiner*—Alex Noguerola
*Attorney, Agent, or Firm*—Fattibene and Fattibene; Arthur T. Fattibene; Paul A. Fattibene

[57] ABSTRACT

A tray having electrodes placed at opposing sides with a sponge placed adjacent each electrode and a gel slab cast there between for use in performing electrophoresis on test samples, such as DNA fragments. An electrophoresis liquid buffer is placed and retained within the sponges preventing the need for immersing the gel slab. The gel slab is cast in place between the sponges, resulting in easier setup. In most cases the time required to perform electrophoresis is reduced. Additionally, unrestrained or free liquid buffer is eliminated, reducing the likelihood of hazardous spills. The combined effect of all these features is a device which is simpler, safer, and more efficient than prior gel electrophoresis devices.

21 Claims, 4 Drawing Sheets

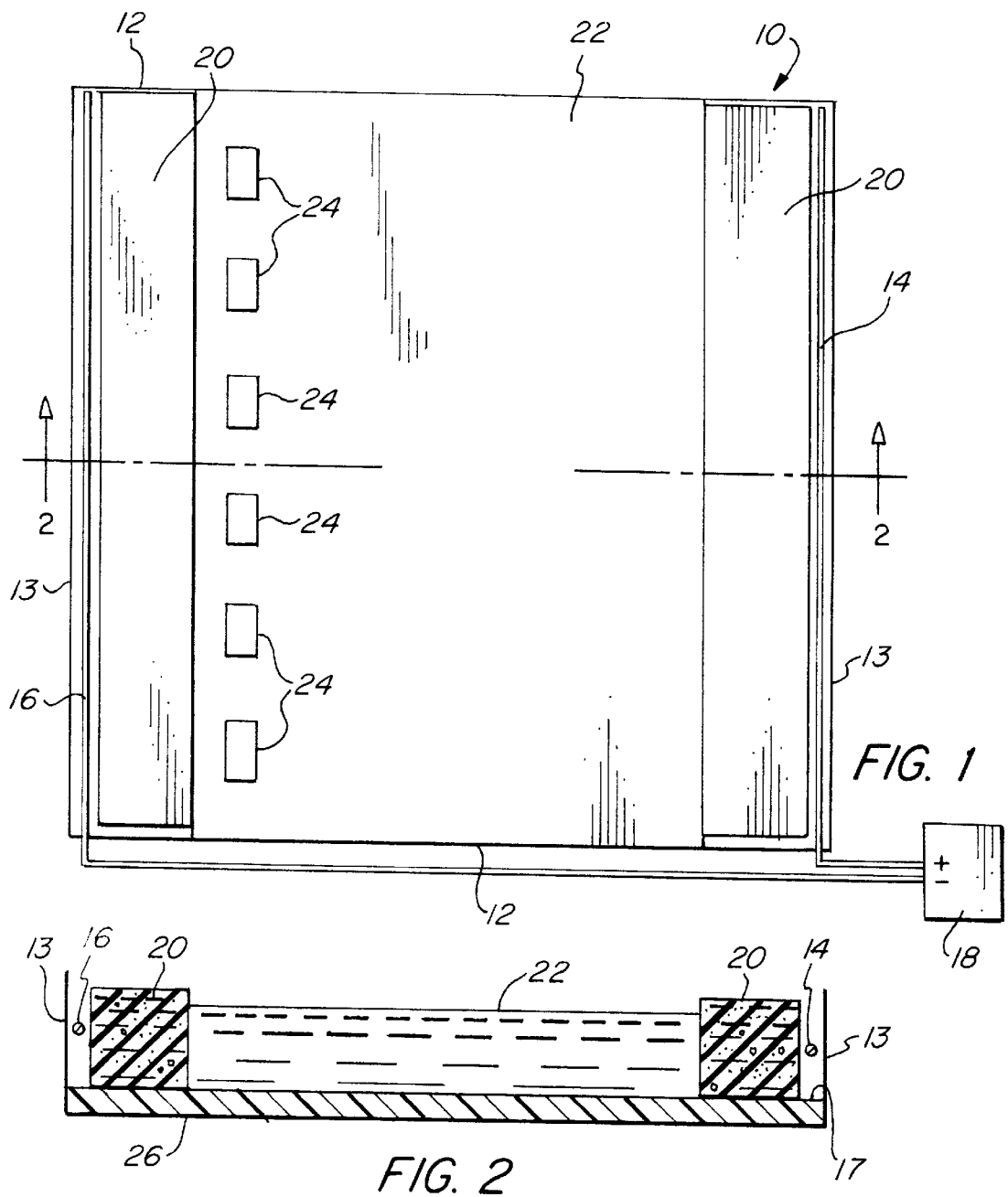

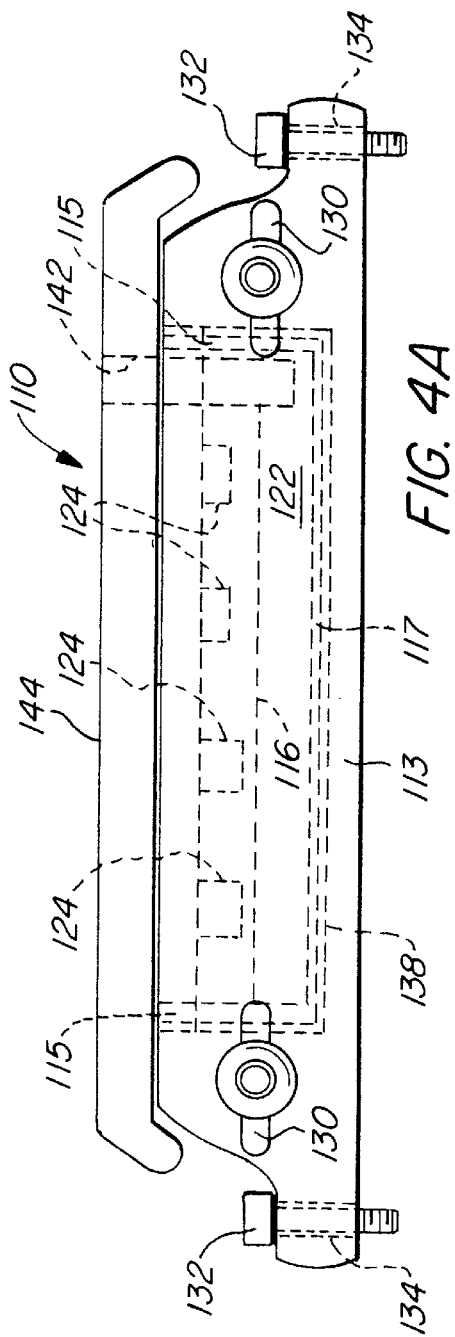
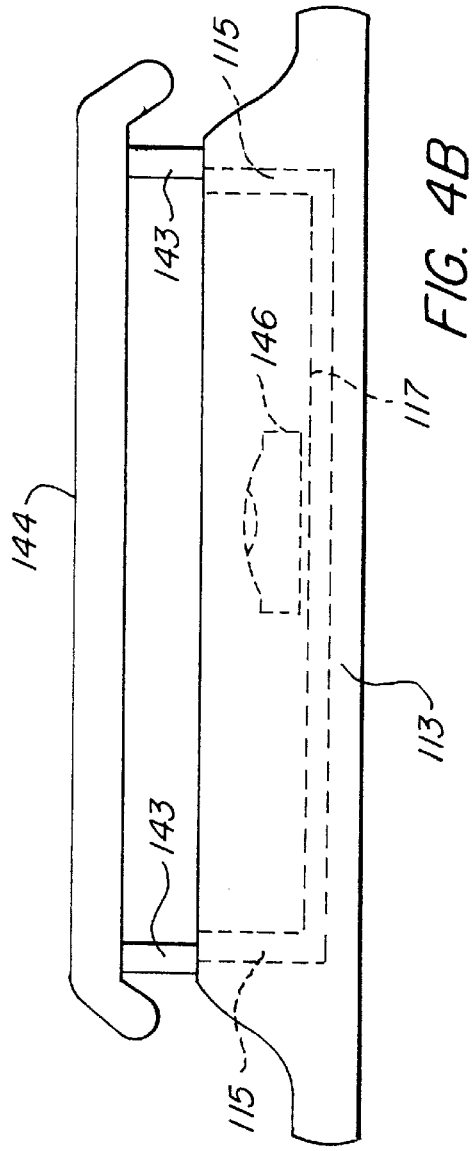

SEMI-DRY ELECTROPHORESIS APPARATUS AND METHOD

FIELD OF THE INVENTION

The present invention relates in general to electrophoresis using a gel and buffer, and more particularly to an electrophoresis device and method using substantially no unretained liquid buffer.

BACKGROUND OF THE INVENTION

Electrophoresis is a relatively old technique and is used to separate, identify, and purify DNA fragments. Electrophoresis techniques are capable of resolving mixtures of DNA fragments that cannot be separated adequately with other sizing procedures, such as density gradient centrifugation. Agarose gel electrophoresis was introduced many years ago, and since then, many different designs of apparatus have been used. Almost all agarose gel electrophoresis is performed on horizontal slab gels, which have several advantages over vertical gels. For example, a relatively low agarose concentration can be used because the entire gel is supported from beneath, gels can be cast in various sizes, and generally the apparatus is usually durable and inexpensive to construct. Gel electrophoresis is generally performed by casting a gel on a glass or plastic plate, or an ultraviolet-transparent (UV-transparent) acrylic gel bed. The plate or gel bed is then installed on a platform so that the gel is submerged just beneath the surface of the liquid electrophoresis buffer. Electrodes are positioned adjacent the edges of the rectangular shaped gel and a voltage difference applied to the electrodes permitting a current to flow through the buffer and gel. The resistance to the passage of electric current of the gel is almost the same as that of the buffer, so a considerable fraction of the applied current passes along the length of the gel. At low voltages, the rate of migration of linear DNA fragments is proportional to the voltage applied and time of application. As the electric field strength is raised, the mobility of high molecular weight fragments of DNA is increased differentially. Accordingly, the effective range of separation of agarose gels decreases as the voltage is increased. Therefore, to obtain maximum resolution of DNA fragments, gels are generally run at a relatively low voltage, which necessarily increases processing time. The location of DNA within the gel can be determined directly by staining. Bands of DNA in the gel are stained with low concentrations of the fluorescent, intercalating dye ethidium bromide. As little as one nanogram of DNA can be detected by direct examination of the gel in ultraviolet light. The electrophoretic migration rate of DNA in agarose gels is dependent upon four main parameters, the molecular size of the DNA, the agarose concentration, the conformation of the DNA, and the applied current.

In recent years, several patents have been granted to devices which purported to improve the gel electrophoresis process. One such prior electrophoresis apparatus and method is disclosed in U.S. Pat. No. 5,582,702 entitled "Apparatus And Method For Electrophoresis" issuing to Cabilly et al on Dec. 10, 1996, which is herein incorporated by reference. Therein disclosed is a substantially closed cassette with a gel contained therein with the ions, cations and anions, required to drive the electrophoretic separation provided by a cation exchange matrix and an anion exchange matrix. The gel, ion exchange matrixes and conductive rods are all in contact and are immersed in a liquid buffer solution. Another device is disclosed in U.S. Pat. No. 5,637,202 entitled "Porous Electrophoresis Sponges" issuing to Harrington et al on Jun. 10, 1997, which is herein incorporated by reference. Therein disclosed is a porous plastic electrophoresis sponge that is intended to replace the gel normally cast in conventional electrophoresis methods. The sponge and attached electrodes are immersed in electrophoresis buffer and used in the same manner as any conventional electrophoresis material. Another device and method is disclosed in U.S. Pat. No. 4,954,236 entitled "Apparatus And Method For Gel Casting And Electrophoresis In A Single Enclosure" issuing to Kushner et al on Sep. 4, 1990, which is herein incorporated by reference. Therein disclosed is an enclosure used to precast gel slabs permitting sealing or subsequent unsealing when the assembly is inserted into a slab type electrophoresis cell designed for gel enclosures with step profiles.

While many of these prior devices function adequately, all require the gels to be submerged in a liquid buffer. Accordingly, many of these devices are difficult to move without spilling buffer, prone to leak electrically-charged buffer, and require that gels be cast in a separate casting device and then relocated to a buffer chamber for performing the gel electrophoresis. Additionally, there is a need to increase efficiencies and simplify the method of performing gel electrophoresis, including decreasing the time required to perform various testing procedures. While these prior patents have advanced the art of electrophoresis, they still require emerging the gel in a buffer solution which has the disadvantages indicated above. Accordingly, there is a continuing need to improve the art of electrophoresis making it simpler and quicker, while reducing the risk of spills of potentially hazardous buffer solutions.

SUMMARY OF THE INVENTION

The present invention comprises a rectangular tray having an anode and a cathode electrode placed at opposing ends of the tray. An elongated sponge is placed adjacent each of the anode and cathode electrodes longitudinally along their length. A space is formed between the sponges for a gel, which may be cast in place. A predetermined amount of liquid buffer solution is applied to the sponges adjacent to the electrodes. Test samples are placed in test wells formed in the gel. A potential difference is applied between the electrodes causing a current to flow through the buffer and the gel. The current causes the test samples placed on the gel to separate in an electrophoresis process.

Accordingly, it is an object of the present invention to reduce the amount of unrestrained liquid buffer used in electrophoresis.

It is a further object of the present invention to provide a more efficient and easier-to-use electrophoresis apparatus and method.

It is an advantage of the present invention that a gel may be precast in place.

It is a further advantage of the present invention that a relatively small amount of liquid buffer is required.

It is a feature of the present invention that sponges are used adjacent each electrode.

It is a further feature of the present invention that the gel is not completely immersed in liquid buffer.

These and other objects, advantages, and features will become readily apparent in view of the following detailed description.

BRIEF DESCRIPTION OF THE DRAWINGS

FIG. 1 is a schematic plan view of one embodiment of the present invention.

FIG. 2 is a schematic cross section taken along line 2—2 in FIG. 1.

FIG. 4A is an elevational view of one side of the embodiment illustrated in FIG. 3.

FIG. 4B is a schematic elevational view of one side of the embodiment illustrated in FIG. 4A showing a raised cover.

DETAILED DESCRIPTION OF THE PREFERRED EMBODIMENTS

Figure 3:
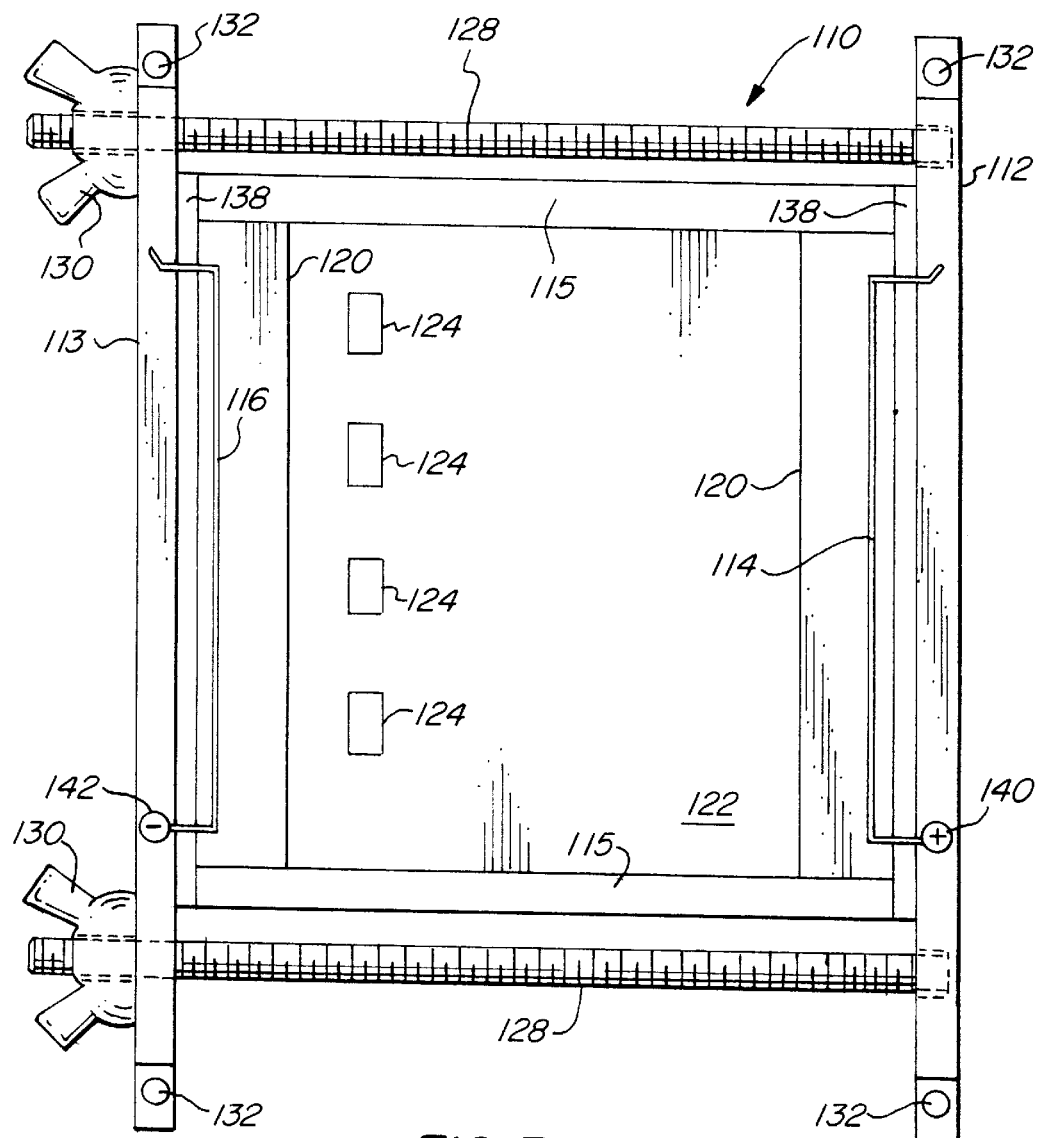
FIG. 3 is a plan view of another embodiment of the present invention.

FIG. 1 schematically illustrates an electrophoresis device 10 according to the present invention. The electrophoresis device 10 comprises a gel bed or tray 12 having four sides. Adjacent to opposing sides 13 are positioned electrodes 14 and 16. Electrode 14 may be an anode connected to a positive terminal of a power source 18. Electrode 16 may be a cathode connected to the negative terminal of power source 18. Adjacent each electrode 14 and 16 is a sponge 20. The sponges 20 extend substantially the entire length of the tray 12. The sponges 20 may be a cellulose sponge, or any well known equivalent sponge or material having the property of holding a liquid. Between the sponges 20 a gel 22 is cast or placed. Wells 24 are formed within the gel 22 and are formed to hold a test sample. The wells 24 may be formed by any conventional method, such as by a standard comb or well-former. Additionally, several rows of wells 24 may be formed so as to permit a larger number of tests in a single gel to be run simultaneously.

FIG. 2 is a cross section taken along line 2—2 in FIG. 1. FIG. 2 more clearly illustrates the sponges 20 placed between the electrodes 14 and 16 and the gel 22. Additionally, as illustrated in FIG. 2, an aluminum cooling block 26 may be used beneath the tray 12 and placed adjacent the tray bottom 17. However, the use of an aluminum cooling block 26 has been found to be unnecessary in nearly all applications, and will generally not needed for the operation of the present invention.

Referring to FIGS. 1 and 2, the basic operation of the present invention can readily be appreciated. The gel 22 may be preferably cast between the sponges 20 or precast and then placed between the sponges 20. A relatively small amount of liquid buffer solution is applied to the sponges 20, soaking them. The buffer solution is restrained or held within the sponges 20, preventing the possibility of spillage and requiring only sufficient buffer to perform the electrophoresis with very little waste. A voltage is then applied between the electrodes 14 and 16 by power source 18, causing a relatively small current to flow. As a result, the test sample, for example DNA fragments, is caused to separate. Various features of the test sample can then be identified using conventional techniques, such as staining, or viewed directly with ultraviolet light.

FIG. 3 is a plan view illustrating another embodiment of the present invention that is adjustable to accommodate different size rectangular gel beds. Accordingly, multiple columns of test sample wells may be utilized in a single gel bed and increased resolution obtained with longer lengths. The electrophoresis device 110 comprises a fixed end side 112 and an opposing adjustable end side 113. Between the fixed end side 112 and the adjustable end side 113 are opposing gel bed sides 115. A threaded rod 128, adjacent each gel bed side 115, has one end fixed within the fixed end side 112 and the other end extending through a bore in the adjustable end side 113. A wing nut 130 is threaded onto each of the threaded rods 128 and is used to secure the gel bed sides 115 between the fixed end side 112 and the adjustable end side 113. Seals or gaskets 138 are attached to adjustable end side 113 and fixed end side 112. These gaskets 138 will make contact with and seal the ends of the gel bed sides 115, so that the gel bed will contain liquid. This permits a combination of different lengths of gel beds to be used, depending upon the application. Placed within and adjacent to the fixed end side 112 is a first electrode 114. Electrode 114 extends through the seal 138. A second electrode 116 is positioned on an opposing side within and adjacent to the adjustable end side 113. Formed within the fixed end side 112 is a connector 140, which may be a banana type electrical connector, for connecting to a positive terminal of a power source. Formed within adjustable end side 113 is a connector 142, which also may be a banana type electrical connector, for connecting to the negative terminal of a power source. Sponges 120 are placed adjacent each electrode 114 and 116 and extend longitudinally along the length of the electrodes 114 and 116. Accordingly, a gel casting area is formed between the sponges 120. The sponges act as a form for casting the gel 122 in place. This saves time and eliminates the need to precast a gel slab and move it. A gel slab 122 having wells 124 therein is illustrated in position between the sponges 120. Placed at each end of the fixed end side 112 and the adjustable end side 113 are adjustable feet 132. The adjustable feet 132 may be threaded through the end sides 112 and 113 and may be used to level the electrophoresis device 110. All of the materials of the electrophoresis device 110 may be made of a non-corrosive plastic material, such as nylon, acrylic, or any equivalent material.

FIG. 4A is an elevational view of the embodiment illustrated in FIG. 3 further including a cover 144. As illustrated in FIG. 4A, the electrode 116 may comprise a platinum wire. The electrode 116 is generally straight. The bubble level may be used in association with the leveling feet 132 to help level the electrophoresis device 110. A bubble level is preferably placed on the gel bed bottom 117 while leveling the gel bed. It is then removed before casting the gel slab 122 on the gel bed. This will facilitate getting a uniform cast of the gel slab 122, as well as improving performance during running. Additionally, the cover 144 may be used to protect the gel slab 122, or to retain heat during some procedures. Another important feature of the cover 144 is to protect a user from electric shock hazards. FIG. 4A also more clearly illustrates the U-shaped tray with gel bed sides 115 and bottom 117. The end of the gel bed sides 115 and the bottom 117 are forced or pressed against the seal 138 on either end of the end sides 113 and 112 by tightening the wing nuts 130. Accordingly, different lengths of U-shaped gel trays may be used for different procedures or for having a gel sufficiently long to accommodate two columns of wells. Different lengths of screws 128, illustrated in FIG. 3, may be used to accommodate the different lengths of U-shaped gel trays.

FIG. 4B is a schematic illustration of the present invention as illustrated in FIG. 4A, but with spacers 143 used to raise or suspend the cover 144 above the adjustable end side 113. By raising or suspending the cover above the gel bed by approximately one half inch or between one and two centimeters, air is allowed to circulate more freely around the gel allowing for dissipation of heat. A bubble level 146 is also illustrated placed on the gel bed bottom 117. After leveling the gel bed, the bubble level 146 is removed and the gel slab is cast.

Figure 5:
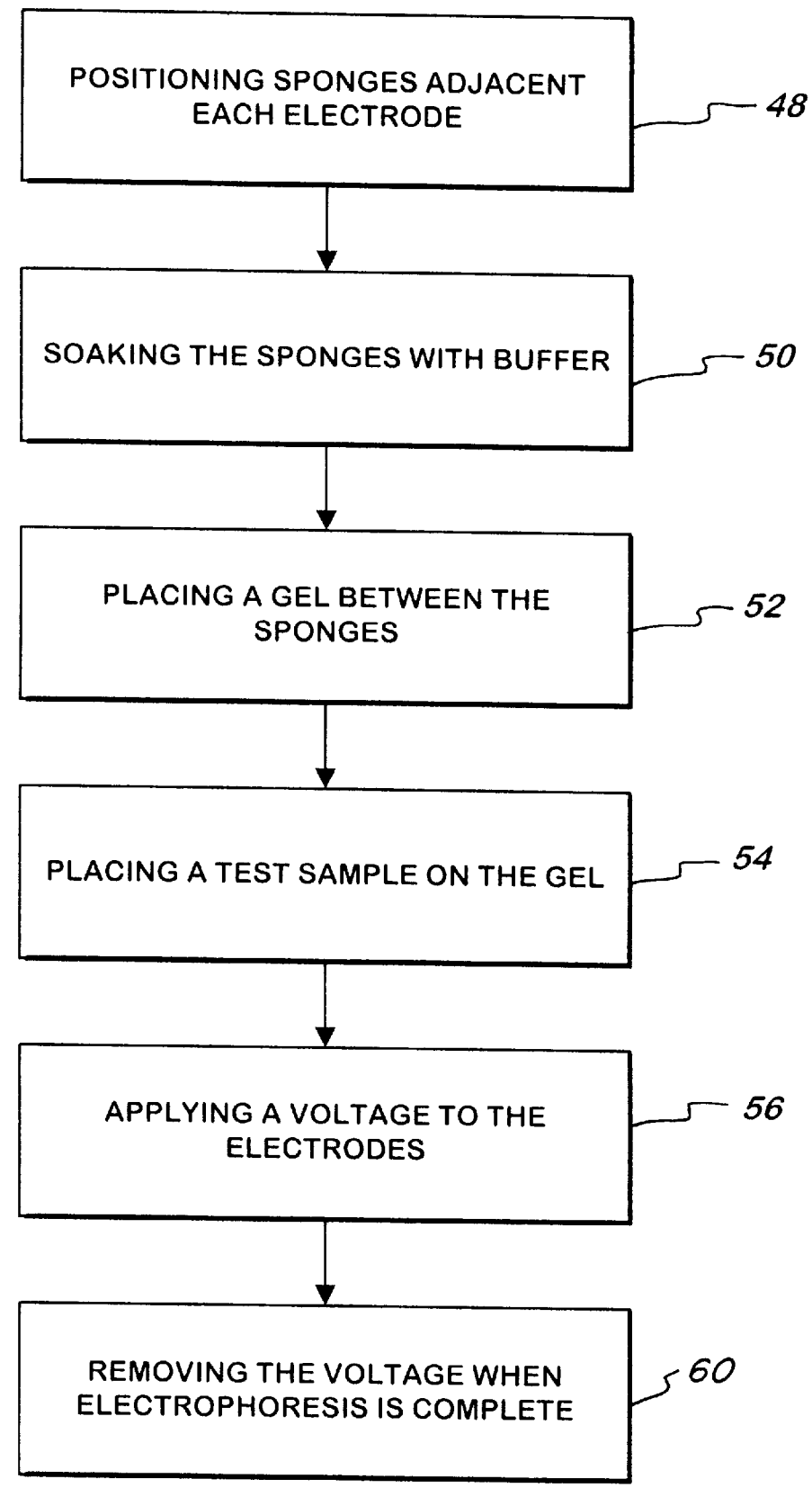
FIG. 5 is a block diagram illustrating the method of the present invention.

FIG. 5 is a block diagram illustrating the method steps or acts in the present invention. Block 48 represents the step of placing or positioning sponges adjacent each electrode. Block 50 represents the step of soaking the sponges with buffer. Block 52 represents the step of casting or placing a gel in the tray between the sponges adjacent each electrode. Block 54 represents the step of placing or putting a test sample on the gel. Block 56 represents the step of applying a voltage to the electrodes causing current to flow there between. Block 60 represents the step of removing the voltage when electrophoresis is complete. The method steps above may be modified slightly and performed in slightly different order, for example the step of soaking the sponges with buffer and the step of casting or placing a gel in the between the sponges may be performed prior to positioning the sponges adjacent each electrode.

A major factor in the success of the device was whether the invention, because it eliminates the reservoir of buffer, would retain sufficient buffer capacity for the duration of an electrophoretic run. If buffer capacity was not adequate, the current flowing through the gel would drop dramatically and the pH of the gel would change drastically, resulting in such deleterious effects as deformed or melted gels, erratic banding patterns, and subsequent unsuccessful electrophoresis. Therefore, various experiments were performed using different parameters to determine the effectiveness of the present invention.

In one experiment, a 1% agarose gel approximately 4 mm thick, using Tris-borate buffer (TBE), was cast between buffer-soaked cellulose sponges on a gel bed approximately 13 cm long. Electrophoresis was performed at 100 Volts for 60 minutes. After standard staining and visualization procedures, it was seen that electrophoresis was successful: the gel appeared similar to a convention gel run submerged under buffer. Buffer capacity, as indicated by the current, remained sufficient during the run.

In another test, a 1% agarose gel approximately 5 mm thick, using Tris-borate buffer (TBE) was cast between buffer-soaked cellulose sponges on a 10 cm long gel bed, forming a gel approximately 6 cm long. A close-fitting cover was also used in this experiment. Electrophoresis was performed at 100 Volts. This gel finished running in approximately 25 minutes, which is somewhat faster than a conventional gel of this size would run. The bands were slightly skewed from top to bottom, however, making them appear somewhat blurry. This experiment was subsequently repeated, but the cover was suspended approximately one-half inch above the top of the gel bed in order to allow air to circulate more freely around the gel. In this experiment the gel ran in the same amount of time, but the bands were much sharper. This showed that placement of the cover is critical in this invention: if placed too close to the gel, heat generated by the electrophoresis will build up around the gel, causing the top surface of the gel to become hotter than the bottom and resulting in skewed bands. When the cover was suspended approximately one half inch above the top of the gel bed, the heat generated was able to dissipate out of the device, resulting in even gel temperatures and sharper banding patterns.

Experiments were also performed to determine how fast the device could run by increasing the running voltage. It was found that a gel cast on a 7.5 mm long bed could be successfully run in 10 minutes at 140 Volts. This is much faster than a conventional gel of that size would run, and the banding patterns were just as sharp. When voltages greater than 150 volts were tested, the device began to overheat and lose buffer capacity before the electrophoresis was completed. Therefore, it was determined that using voltages up to approximately 150 volts, the device has the distinct advantage of significantly decreasing the running time of gel electrophoresis procedures.

Experiments were also performed to determine the effectiveness of various sponge materials. All brands and varieties of cellulose sponges tried were found to perform about equally well. Other experiments were performed using Tris-acetate buffer (TAE) instead of TBE. This buffer was found to work well; however, it was found that lower voltages and slower running times were required with this buffer than could be used with TBE.

In all the foregoing experiments, the total amount of buffer retained in the sponges was approximately 25–30 ml. This is about one-tenth or less of the amount of buffer needed to run a conventional gel electrophoresis system. Thus, the present invention drastically reduces the amount of buffer needed to perform gel electrophoresis, while keeping this small amount of buffer safely retained within sponges so that it cannot spill from the system.

Accordingly, the results of the experiments conducted confirm the practicality and advantages of the present invention. The advantages over conventional gel electrophoresis systems include: significantly reduced electrophoresis times; a cast-in-place gel electrophoresis system that facilitates processing of the gel; and a gel electrophoresis system which uses sponges to retain a small yet sufficient amount of buffer, preventing liquid buffer from spilling or splashing and allowing just a small amount of buffer to be used. These advantages are provided in a relatively simple device and method that may be easily practiced.

While the present invention has been described with respect to several preferred embodiments, it should be appreciated that various modifications may be made without departing from the spirit and scope of this invention.

What is claimed is:

1. A semi-dry electrophoresis system comprising:

a tray having sides and a bottom;

a first electrode placed adjacent one of the sides of said tray;

a second electrode placed adjacent another of the sides of said tray, said second electrode opposing said first electrode; and a pair of sponges, one of said pair of sponges placed adjacent said first electrode and the other of said pair of sponges placed adjacent said second electrode, said pair of sponges placed on the bottom of said tray, and capable of containing a predetermined amount of liquid buffer and having a space there between;

gel containing a test sample placed in the space between said pair of sponges such that surfaces of the gel substantially perpendicular to the bottom surface contact a surface of each of said pair of sponges, whereby a contact surface is obtained perpendicular to an applied electric field, whereby a voltage may be applied to said first and second electrodes forming the applied electric field for performing electrophoresis.

2. A semi-dry electrophoresis system as in claim 1 wherein:

said pair of sponges are a pair of cellulose sponges.

3. A semi-dry electrophoresis system as in claim 1 wherein:

the gel is an agarose gel.

4. A semi-dry electrophoresis system as in claim 1 wherein:

the predetermined amount of liquid buffer is tris-acetate.

5. A semi-dry electrophoresis system as in claim 1 wherein:

the predetermined amount of liquid buffer is tris-borate.

6. A semi-dry electrophoresis system as in claim 1 further comprising:

leveling feet placed on said tray.

7. A semi-dry electrophoresis system as in claim 6 further comprising:

a cover placed over said tray; and a bubble level placed on said tray.

8. A semi-dry electrophoresis system as in claim 7 further comprising:

spacers placed between said cover and said tray.

9. A semi-dry electrophoresis system as in claim 1 wherein:

said electrode is a platinum wire.

10. An apparatus for use in performing electrophoresis analysis of a sample to be tested comprising:

a tray having four sides and a bottom;

a first electrode having a longitudinal length placed adjacent one of the four sides of said tray;

a second electrode having a longitudinal length placed adjacent another of the four sides of said tray, said second electrode opposing said first electrode;

a first sponge placed adjacent the longitudinal length of said first electrode and having a first surface substantially perpendicular to the bottom of said tray;

a second sponge placed adjacent the longitudinal length of said second electrode and having a second surface substantially perpendicular to the bottom of said tray, and facing said first surface, a space being formed between the first and second surfaces of said first and second sponges;

a first predetermined amount of liquid buffer placed within said first sponge;

a second predetermined amount of liquid buffer placed within said second sponge;

a gel placed between the first and second surfaces of said first and second sponge within the space; and a power source connected between said first and second electrodes, whereby a test sample may be placed on said gel and a voltage applied to said first and second electrodes with said power source for performing electrophoresis resulting in analysis of the test sample.

11. An apparatus for use in performing electrophoresis analysis as in claim 10 wherein:

said first and second sponges are cellulose sponges.

12. An apparatus for use in performing electrophoresis analysis as in claim 10 further comprising:

leveling feet placed on said tray.

13. An apparatus for use in performing electrophoresis analysis as in claim 12 further comprising:

a cover placed over said tray.

14. An apparatus for use in performing electrophoresis analysis of a DNA sample to be tested comprising:

a U-shaped gel tray having two opposing sides and a bottom;

a fixed end side placed adjacent one end of said U-shaped gel tray;

a pair of screws held within said fixed end side, each of said pair of screws having a length longer than said U-shaped gel tray;

an adjustable end side having a pair of holes therein placed adjacent another side of said U-shaped gel tray, said pair of holes adapted to receive said pair of screws;

a first seal placed between said U-shaped gel tray and said fixed end side;

a second seal placed between said U-shaped gel tray and said adjustable end side;

a pair of wing nuts, one each of said pair of wing nuts threaded onto one each of said pair of screws, whereby said U-shaped gel tray is held securely against said first and second seals and said fixed and adjustable end side;

a first wire electrode having a first longitudinal length and placed adjacent said fixed end side;

a second wire electrode having a second longitudinal length and placed adjacent said adjustable end side, said second electrode opposing said first electrode;

a first sponge placed adjacent the first longitudinal length of said first wire electrode;

a second sponge placed adjacent the second longitudinal length of said second wire electrode, forming a space between said first and second sponges;

a first predetermined amount of liquid buffer placed within said first sponge;

a second predetermined amount of liquid buffer placed within said second sponge;

an agarose gel placed in the space between said first and second sponge, said agarose gel having a column of test wells formed therein;

a cover placed over said U-shaped gel tray;

a bubble level placed on the apparatus;

a first pair of adjustable leveling feet formed in said fixed end side;

a second pair of adjustable leveling feet formed in said adjustable end side; and a voltage power source connected between said first and second electrodes, whereby the DNA sample may be placed in the column of test wells and a voltage applied by said voltage power source to said first and second wire electrodes for performing electrophoresis resulting in banding and analysis of the DNA sample.

15. A method of performing electrophoresis comprising the steps of:

positioning a sponge adjacent each opposing electrode, such that a surface of each sponge is opposing each other;

soaking the sponges with a buffer;

placing a gel between the opposing surfaces of the sponges;

putting a test sample on the gel; and applying a voltage to the electrodes.

16. A method of performing electrophoresis as in claim 15 wherein:

the sponges are cellulose sponges.

17. A method of performing electrophoresis as in claim 15 wherein:

the step of applying a voltage has a duration of less than thirty minutes.

18. A method of performing electrophoresis as in claim 15 wherein:

the step of soaking provides only sufficient buffer to be absorbed and retained by the sponges.

19. A method of performing electrophoresis as in claim 15 further comprising:

suspending a cover over the gel, whereby air is allowed to circulate freely around the gel.

20. An apparatus for use in performing electrophoresis analysis of a sample to be tested comprising:

a U-shaped gel tray having two opposing sides and a bottom;

a fixed end side placed adjacent one end of said U-shaped gel tray;

a pair of screws held within said fixed end side, each of said pair of screws having a length longer than said U-shaped gel tray;

an adjustable end side having a pair of holes therein placed adjacent another side of said U-shaped gel tray, said pair of holes adapted to receive said pair of screws;

a first seal placed between said U-shaped gel tray and said fixed end side;

a second seal placed between said U-shaped gel tray and said adjustable end side;

a pair of nuts, one each of said pair of nuts threaded onto one each of said pair of screws, whereby said U-shaped gel tray is held securely against said first and second seals and said fixed and adjustable end side;

a first wire electrode having a first longitudinal length and placed adjacent said fixed end side;

a second wire electrode having a second longitudinal length and placed adjacent said adjustable end side, said second electrode opposing said first electrode;

a first sponge placed adjacent the first longitudinal length of said first wire electrode;

a second sponge placed adjacent the second longitudinal length of said second wire electrode, forming a space between said first and second sponges;

a first predetermined amount of liquid buffer placed within said first sponge;

a second predetermined amount of liquid buffer placed within said second sponge;

a gel placed in the space between said first and second sponge, said gel having a column of test wells formed therein;

a cover placed over said U-shaped gel tray; and a voltage power source connected between said first and second electrodes, whereby the sample may be placed in the column of test wells and a voltage applied by said voltage power source to said first and second wire electrodes for performing electrophoresis resulting in banding and analysis of the sample.

21. An apparatus for use in performing electrophoresis analysis of a sample to be tested comprising:

a U-shaped gel tray having two opposing sides and a bottom;

a fixed end side placed adjacent one end of said U-shaped gel tray;

a pair of fasteners held within said fixed end side, each of said pair of fasteners having a length longer than said U-shaped gel tray;

an adjustable end side having a pair of holes therein placed adjacent another side of said U-shaped gel tray, said pair of holes adapted to receive said pair of fasteners;

a first seal placed between said U-shaped gel tray and said fixed end side;

a second seal placed between said U-shaped gel tray and said adjustable end side;

a pair of fastener attachments, one each of said pair of fastener attachments attaching onto one each of said pair of fasteners, whereby said U-shaped gel tray is held securely against said first and second seals and said fixed and adjustable end side;

a first wire electrode having a first longitudinal length and placed adjacent said fixed end side;

a second wire electrode having a second longitudinal length and placed adjacent said adjustable end side, said second electrode opposing said first electrode;

a first sponge placed adjacent the first longitudinal length of said first wire electrode;

a second sponge placed adjacent the second longitudinal length of said second wire electrode, forming a space between said first and second sponges;

a cover placed over said U-shaped gel tray; and a voltage power source connected between said first and second electrodes, whereby a voltage applied by said voltage power source to said first and second wire electrodes for performing electrophoresis results in banding and analysis of a sample.

* * * * *